US00PP31131P2

(12) United States Plant Patent
Bergman

(10) Patent No.: US PP31,131 P2
(45) Date of Patent: Nov. 26, 2019

(54) ***CHRYSANTHEMUM* PLANT NAMED 'CIDZ0092'**

(50) Latin Name: ***Chrysanthemum* x *morifolium***
Varietal Denomination: CIDZ0092

(71) Applicant: SYNGENTA PARTICIPATIONS AG, Basel (CH)

(72) Inventor: Wendy R. Bergman, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,515

(22) Filed: Nov. 27, 2018

(51) Int. Cl.
*A01H 5/02* (2018.01)
*A01H 6/14* (2018.01)

(52) U.S. Cl.
USPC ..... Plt./293

(58) Field of Classification Search
USPC ..... Plt./263.1, 284, 286, 287, 292, 293
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Chrysanthemum* plant named 'CIDZ0092' having red, decorative-type inflorescences, excellent flower production, strong growth and spreading plant habit, and very uniform flowering with response time of 8 weeks when grown under short days.

1 Drawing Sheet

Latin name of the genus and species of the plant claimed: *Chrysanthemum* x *morifolium*.

Varietal denomination: 'CIDZ0092'.

BACKGROUND OF THE NEW PLANT

The present invention comprises a new *Chrysanthemum*, botanically known as *Chrysanthemum* x *morifolium*, and hereinafter referred to by the variety name 'CIDZ0092'.

'CIDZ0092' is a product of a planned breeding program. The new cultivar has red, decorative-type inflorescences, excellent flower production, strong growth and spreading plant habit, and very uniform flowering with response time of 8 weeks when grown under short days.

'CIDZ0092' originates as a natural whole plant mutation discovered among flowering plants of the variety 'B8148' growing in a greenhouse in Gilroy, Calif. in November 2015.

The parent is the proprietary unpatented breeding line 'B8148', and having inflorescences of a purple hue under usual conditions, while 'CIDZ0092' differs having red inflorescences.

The first act of asexual reproduction of 'CIDZ0092' was accomplished when vegetative cuttings were propagated from the initial selection in February 2016 in a greenhouse in Gilroy, Calif.

BRIEF SUMMARY OF INVENTION

Horticultural examination of plants grown from cuttings of the plant initiated February 2016, and continuing thereafter, has demonstrated that the combination of characteristics as herein disclosed for 'CIDZ0092' are firmly fixed and are retained through successive generations of asexual reproduction.

'CIDZ0092' has not been observed under all possible environmental conditions. The phenotype may vary significantly with variations in environment such as temperature, light intensity and day length.

A Plant Breeder's Right for this cultivar was applied for in Canada on Nov. 19, 2018, No. 15583. 'CIDZ0092' has not been made publicly available prior to the effective filing date of this application, notwithstanding any disclosure that may have been made less than one year prior to the effective filing date of this application by the inventor or another who obtained 'CIDZ0092' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0092' with colors being as true as possible with an illustration of this type. The photographic drawings show in FIG. 1 a close-up view of the inflorescence of the new variety and in FIG. 2 a whole flowering plant grown in a greenhouse.

DETAILED BOTANICAL DESCRIPTION

The plant descriptions and measurements were taken indoors in Gilroy, Calif. in November 2018 on about 12 week old plants. Unrooted cuttings had been planted, 5 plants per pot, in 6 inch pots on Aug. 22, 2018. The plants were pinched and moved to short days on Sep. 19, 2018 to induce flowering.

Figure 1:
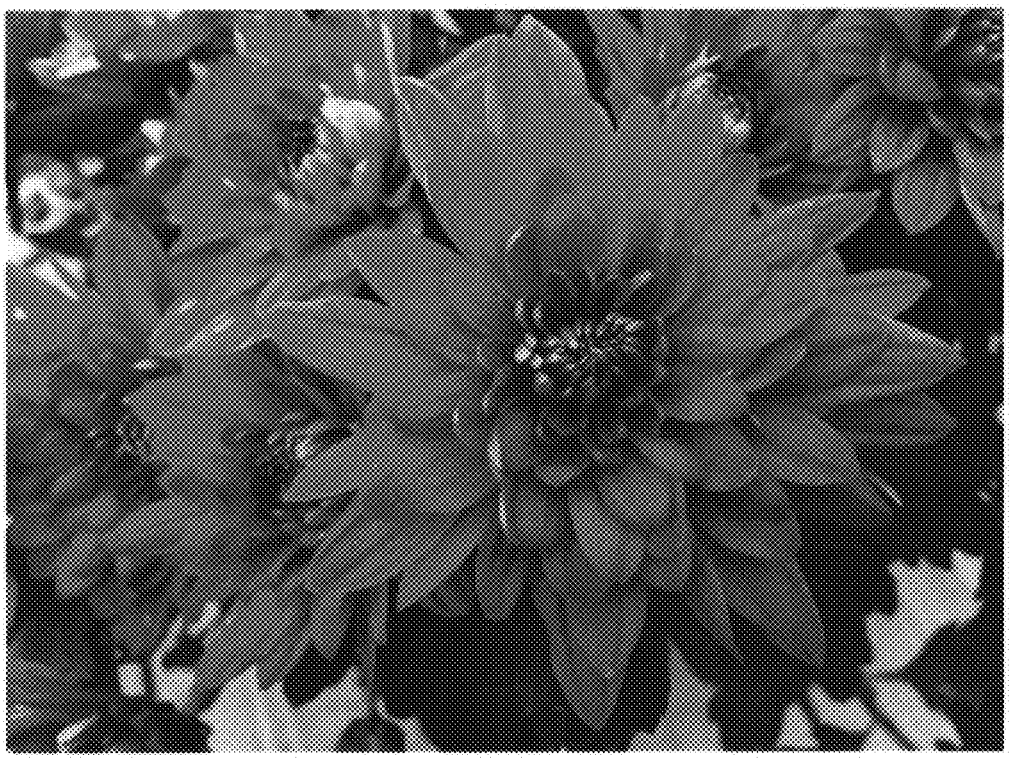
Figure 2:
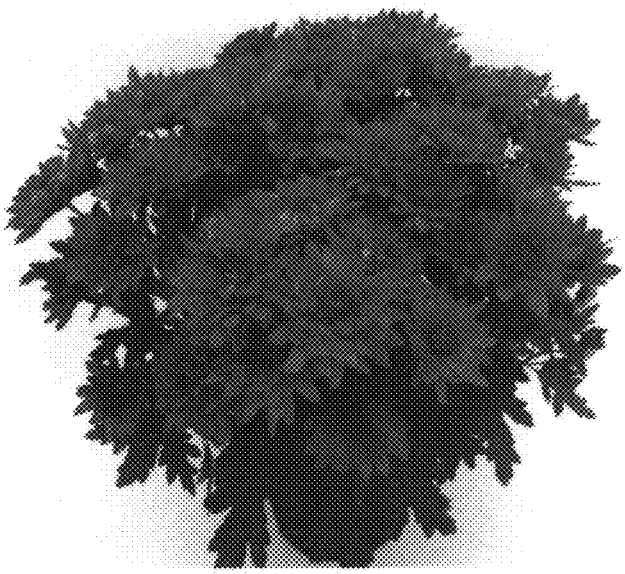

The aforementioned photographs: FIGS. 1 and 2 was taken in Gilroy, Calif. in November 2018, and showing a plant from a trial, in which flowering had been induced by applying black cloth.

These plants were about 12 weeks of age. Unrooted cuttings had been planted, 4 plants per pot, in 6 inch pots. The plants were pinched and moved to short days to induce flowering.

Color references are made to The Royal Horticultural Society Colour Chart (R.H.S.) 2001.

TABLE 1

DIFFERENCES BETWEEN THE NEW VARIETY 'CIDZ0092' AND A MOST SIMILAR VARIETY:

| | 'CIDZ0092' | 'YOTOBAGO' (U.S. Plant Pat. No. 15,412) |
|---|---|---|
| Plant height: | Shorter | Taller |
| Flower size: | Larger | Smaller |
| Flower response: | Faster | Slower |

Plant:

*Form, growth and habit.*—Herbaceous pot-type, stems upright, freely branching, strong and moderately vigorous growth habit.

*Plant height.*—27-28 cm.

*Plant height (inflorescence included).*—30-32 cm.

*Plant width.*—26-33 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 136A.

*Lower surface.*—Between RHS 137C.

*Mature, leaf color, upper surface.*—Closest to RHS NN137A.

*Lower surface.*—RHS 137B.

*Length.*—7.5-8.5 cm.

*Width.*—5.0-5.5 cm.

*Shape.*—Obovate.

*Base shape.*—Attenuate.

*Apex shape.*—Mucronulate.

*Margin.*—Lobed; somewhat serrate.

*Texture, upper surface.*—Small hairs.

*Lower surface.*—Small hairs.

*Color of veins, upper surface.*—RHS 138B.

*Color of veins, lower surface.*—RHS 137C.

*Pattern of veining.*—Palmate.

*Petiole color.*—RHS 137A.

*Length.*—0.7-1.2 cm.

*Diameter.*—0.2 cm.

*Texture.*—Small hairs.

Stem:

*Quantity of main branches per plant.*—4-5.

*Color of stem.*—RHS 138A.

*Length of stem.*—19-22 cm.

*Diameter.*—0.3-0.5 cm.

*Length of internodes.*—1.5-2.0 cm.

*Texture.*—Small hairs.

*Color of peduncle.*—RHS NN137A.

*Length of peduncle.*—3.5-6.0 cm.

*Peduncle diameter.*—0.2 cm.

*Texture.*—Some hairs.

Inflorescence:

*Type.*—Compositae type, double-type inflorescences borne terminally above foliage, ray florets arranged acropetally on a capitulum.

*Quantity of short days to flowering (response time).*—8 weeks.

*Natural season flowering.*—Not determined on this variety.

*Quantity of inflorescences per plant.*—25-30.

*Lastingness of individual blooms on the plant.*—4 weeks.

*Fragrance.*—Some daisy smell.

Bud (just when opening/showing color):

*Color.*—Closest to RHS 59A.

*Length.*—1.2-1.4 cm.

*Width.*—1.1-1.3 cm.

*Shape.*—Oblate.

Immature inflorescence:

*Diameter.*—3.5-6.0 cm.

*Color of ray florets, upper surface.*—RHS 59C.

*Lower surface.*—RHS 186D.

Mature inflorescence: Not fully open.

*Diameter.*—7.0-7.5 cm.

*Depth.*—1.8-2.1 cm.

*Total diameter of disc.*—0.4-0.6 cm.

*Receptacle color.*—RHS 145B.

*Receptacle height.*—0.4 cm.

*Receptacle diameter.*—0.5 cm.

Ray florets:

*Average quantity of florets.*—150-170.

*Color of ray florets, upper surface.*—RHS 60A.

*Lower surface.*—RHS 186C.

*Length.*—1.4-3.0 cm.

*Width.*—0.2-1.1 cm.

*Shape.*—Eliptical.

*Apex shape.*—Acute.

*Margin.*—Entire.

*Texture, upper surface.*—Smooth.

*Lower surface.*—Smooth.

Disc florets:

*Average quantity of florets.*—40-45.

*Color of florets.*—RHS 13A apex, RHS 145C at the base.

*Length.*—0.4 cm.

*Width.*—0.1 cm.

*Shape.*—Tubular, elongated.

*Apex shape.*—Acute, 5 pointed.

Phyllaries:

*Quantity.*—18-23.

*Color, upper surface.*—RHS 136A.

*Lower surface.*—RHS 136B.

*Length.*—0.7-0.9 cm.

*Width.*—0.2-0.3 cm.

*Shape.*—Lanceolate.

*Apex shape.*—Acute.

*Base.*—Fused.

*Margins.*—Entire; slightly papery.

*Texture, upper surface.*—Hairs.

*Lower surface.*—Smooth.

Reproductive organs:

*Pistil.*—1, found on both types of florets.

*Length.*—0.6 cm.

*Style color.*—RHS 155C.

*Style length.*—0.4 cm.

*Stigma color.*—RHS 177A.

*Stigma shape.*—Bi-parted.

*Ovary color*.—RHS 155C but more translucent.
*Stamens*.—4, found only on the disc florets, very few.
*Color of filaments*.—RHS 155C.
*Length filaments*.—0.4-0.5 cm.
*Anther color*.—RHS 15A.
*Anther length*.—0.15 cm.
*Anther shape*.—Oval.
*Color of pollen*.—RHS 17A.
*Pollen amount*.—Sparse.
*Fertility/seed set*.—Has not been observed to date.
*Disease/pest resistance*.—Has not been observed to date.

What is claimed is:

1. A new and distinct variety of *Chrysanthemum* plant named 'CIDZ0092' substantially as illustrated and described herein.

* * * * *